United States Patent [19]

Johnson et al.

[11] Patent Number: 5,136,085

[45] Date of Patent: Aug. 4, 1992

[54] SYNTHESIS OF 2-AMINOBENZOPHENONES

[75] Inventors: Marty C. Johnson, Mebane; Stephen V. Frye, Durham, both of N.C.

[73] Assignee: Glaxo Inc., Research Triangle Park, N.C.

[21] Appl. No.: 725,698

[22] Filed: Jul. 3, 1991

Related U.S. Application Data

[62] Division of Ser. No. 619,147, Nov. 28, 1990, Pat. No. 5,053,543.

[51] Int. Cl.$^5$ ............................................. C07C 259/06
[52] U.S. Cl. .................................... 560/315; 540/544; 544/63; 548/240; 564/183; 564/184; 564/185; 564/186
[58] Field of Search ............... 564/183, 163, 186, 184, 564/185; 560/315; 540/544; 544/63; 548/240

[56] References Cited

U.S. PATENT DOCUMENTS

| | | | |
|---|---|---|---|
| 2,893,992 | 7/1959 | Sternbach et al. | 260/239 |
| 3,051,701 | 8/1962 | Reeder et al. | 260/239 |
| 3,106,587 | 10/1963 | Harms et al. | 260/618 |
| 3,136,815 | 6/1964 | Reeder et al. | 260/562 |
| 3,202,661 | 8/1965 | Brust et al. | 260/288 |
| 3,203,990 | 8/1965 | Keller et al. | 260/570 |
| 3,239,564 | 3/1965 | Reeder et al. | 260/570 |
| 3,243,430 | 3/1966 | Metlesics et al. | 260/239 |
| 3,261,870 | 7/1966 | Rachlin et al. | 260/591 |
| 3,267,110 | 8/1966 | Pachter et al. | 260/296 |
| 3,297,755 | 1/1967 | Sternbach et al. | 260/566 |
| 3,341,592 | 9/1967 | Sternbach et al. | 260/570 |
| 3,609,146 | 11/1968 | Houlihan | 260/239 |
| 3,651,046 | 3/1972 | Dereig et al. | 260/239 |
| 3,686,308 | 8/1972 | Ning et al. | 260/562 |
| 3,740,442 | 6/1973 | Ott et al. | 424/330 |
| 4,093,734 | 6/1978 | Kruger et al. | 424/274 |
| 4,175,184 | 11/1979 | Merkle et al. | 544/10 |
| 4,421,931 | 12/1983 | Tonne et al. | 564/139 |
| 4,820,834 | 4/1988 | Evans et al. | 540/504 |

FOREIGN PATENT DOCUMENTS

500916 7/1930 Fed. Rep. of Germany ............ 12/5

OTHER PUBLICATIONS

Sternbach, Angew. Chem. Int. Ed. Engl. 1971, 10,34.
Walsh, Synthesis, Sep. 1980, 677–688.
Fryer, "Ligand Interactions at the Benzodazepine", Comprehensive Medicinal Chemistry, vol. 3, 539–566.
Nahm, Tetrahedron Letter, vol. 22, No. 39, 3815-3813 (1981).
Clack et al., Journal of Organic Chemistry, vol. 9, 55-57 (1943).
Stephen V. Frye et al., Journal of Organic Chemistry, vol. 56, 1991.

*Primary Examiner*—Richard L. Raymond
*Assistant Examiner*—Brian M. Burn
*Attorney, Agent, or Firm*—David J. Levy

[57] ABSTRACT

Process for synthesizing 2-aminobenzophenones such as the following formula (I):

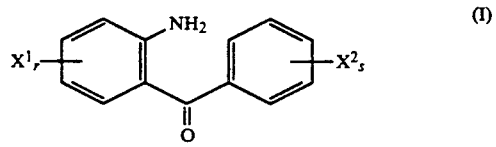

wherein $X^1$ and $X^2$ are substituents and r and s are 1 or 2, by reacting an anthranilic acid amide e.g. an N-alkoxy-N-alkyl anthranilic acid amide, with a halobenzene in the presence of an alkyllithium reagent.

5 Claims, No Drawings

SYNTHESIS OF 2-AMINOBENZOPHENONES

This is a division of U.S. Ser. No. 07/619,147, filed Nov. 28, 1990, now U.S. Pat. No. 5,053,543.

BACKGROUND OF THE INVENTION

2-Aminobenzophenones are important intermediates in the synthesis of the benzodiazephine class of pharmaceuticals as well as other products as described by Leo H. Sternbach in Angew. Chem. Int. Ed. Engl. 1971, 10, 34 and in reviews including that by David A. Walsh in Synthesis, September 1980 pp. 677–688. Benzodiazepines such as diazepam and chlordiazepoxide are useful as anxiolytics, minor tranquilizers and antagonists of gastrin and cholecystokinin for treating disorders of the gastrointestinal, central nervous and appetite regulatory systems of mammals. References to these activities include the following U.S. Patents:

| | | |
|---|---|---|
| 2,893,992 | 3,243,430 | 3,651,046 |
| 3,051,701 | 3,261,870 | 3,686,308 |
| 3,136,815 | 3,267,110 | 3,740,442 |
| 3,202,661 | 3,297,755 | 4,820,834 |
| 3,203,990 | 3,341,592 | |
| 3,239,564 | 3,609,146 | |

The particular structural features of benzodiazepines which influence activity are described in the chapter "Ligand Interactions at the Benzodiazepine Receptor" by R. Ian Fryer in Comprehensive Medicinal Chemistry, pp. 539–566, Vol. 3, Ed. by John C. Emmett, Pergamon Press, Oxford (1990).

It is known that N-methoxy-N-methylamides combine with Grignard reagents and organolithium species in tetrahydrofuran to form ketones as described by Steven Nahm and Steven M. Weinreb in Tetrahedron Letter, Vol. 22, No. 39, pp. 3815–3813 (1981).

It is an object of the present invention to provide a facile high yield synthesis for 2-aminobenzophenones which is applicable with a wide variety of substituents.

SUMMARY OF THE INVENTION

It has been found that reaction of an anthranilic acid amide with a halobenzene in the presence of an alkyllithium results in the alkyllithium reacting preferentially with the halobenzene to form a phenyllithium which then reacts with the amide to form a ketone rather than with the amide directly.

The invention comprises a process for producing a 2-aminobenzophenone which is either unsubstituted or is substituted on the phenyl rings thereof, which comprises reacting;

i) an N-alkoxy-N-alkyl anthranilic acid amide or such where the alkoxy and alkyl groups are joined, which amide is either unsubstituted or is substituted on the phenyl ring thereof; and ii) a halobenzene which is either unsubstituted or is substituted on the phenyl ring thereof, in the presence of an alkyllithium compound.

Also part of the invention are novel intermediates.

DETAILED DESCRIPTION OF THE INVENTION

More particularly, the invention comprises a process for producing a 2-aminobenzophenone of the following formula (I):

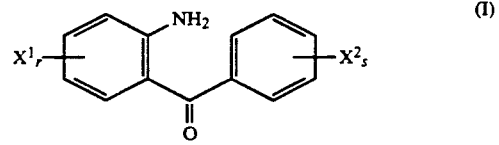

wherein
- $X^1$ is independently hydrogen, trifluoromethyl, cyano, hydroxy, loweralkyl, chlorine, fluorine, loweralkylthio, loweralkoxy, —Y—COOR$^1$ or —Y—NR$^2$R$^3$;
- $X^2$ is independently a value of $X^1$;
- Y is a direct bond or a $C_{1-4}$ linear or branched divalent alkyl;
- $R^1$ is loweralkyl, cycloloweralkyl, substituted or unsubstituted phenyl or (substituted or unsubstituted phenyl)loweralkyl wherein the phenyl or phenylloweralkyl substituents may be 1 or 2 of chlorine, fluorine, loweralkyl, loweralkoxy, nitro or trifluoromethyl;
- $R^2$ and $R^3$ are independently a value of $R^1$ or in combination with the N of the NR$^2$R$^3$ group form an unsubstituted or mono or disubstituted, saturated or unsaturated, 4–7 membered heterocyclic ring or benzofused 4–7 membered heterocyclic ring, or said heterocyclic ring or said benzofused heterocyclic ring further comprises a second heteroatom selected from O and NCH$_3$ and the substitution is independently selected from $C_{1-4}$ alkyl;
- r is 1 or 2; and
- s is 1 or 2, which comprises:
  reacting an anthranilic acid amide of the following formula (II) with a halobenzene of the following formula (III):

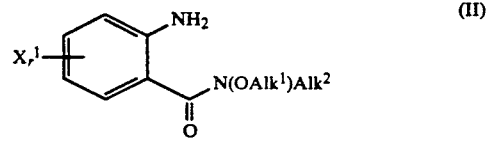

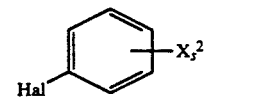

wherein
- Alk$^1$ and Alk$^2$ are independently $C_{1-4}$ alkyl or are joined to each other to form a 5–7 membered saturated ring with the nitrogen and oxygen atoms to which they are attached and
- Hal is bromine or iodine, in the presence of an alkyllithium compound.

As used herein, "lower alkyl" e.g. as part of loweralkoxy, means alkyl of about 1 to 6 carbons; and r and s may be 1 or 2 meaning 1 or 2X$^1$ or X$^2$ substituents on the phenyl rings.

The reaction conditions for the process of the invention can be adjusted according to the reactivities of the particular starting materials and reagant chosen. Thus, a reaction temperature of about −70° to −100° C. and the use of an inert solvent such as an ether, e.g. tetrahydrofuran, may be employed in most cases. The molar ratio may vary although a 1:1 ratio of N-alkoxy-N-alkyl anthranilic acid amide: halobenzene, e.g. formula (II):-(III) is most appropriate.

The amount of alkyl lithium employed is at least 1 equivalent although about 2 equivalents is preferred since the alkyl lithium reagent or the intermediary phenyl lithium reagent, e.g. the reaction product of the alkyl lithium and the halobenzene (III), will react to some extent with the —NH$_2$ group of the anthranilic acid, e.g. of formula (II), and tie up that portion of the reagent. Thus, extra lithium reagent is usually appropriate whereby an appropriate molar ratio of formula (II): formula (III): alkyl lithium reagent is about 1:1:2. Examples of alkyl lithium reagents include methyl, ethyl, propyl, n-butyl, sec-butyl, t-butyl and n-pentyl lithium.

Formula (II) starting materials can be produced according to the following overall Reaction Scheme 1:

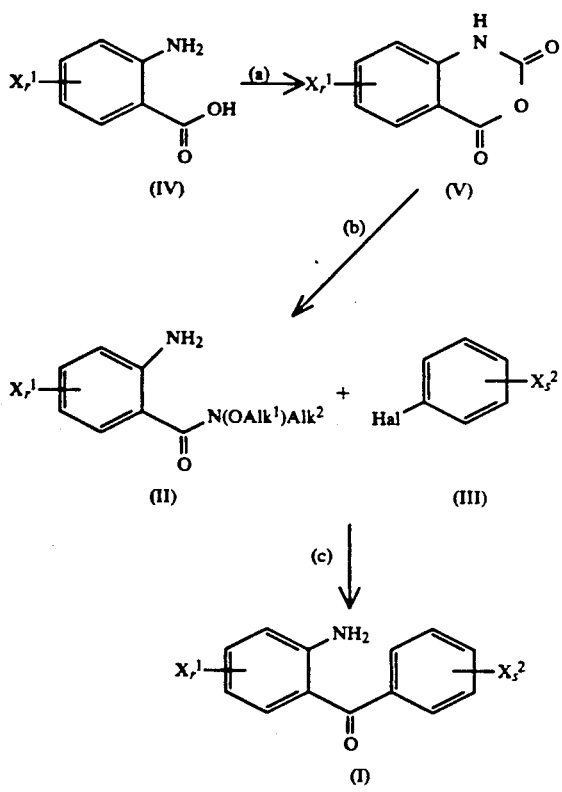

In formulae (II), (III), (IV) and (V), $X^1$, $X^2$, r and s are as defined for Formula (I) above while Alk$^1$ and Alk$^2$ are as defined for formula (II), e.g. methyl, ethyl or sec-butyl and Hal is bromine or iodine with bromine being a particular halogen.

In Reaction Scheme 1, step (a) is shown as enablement for the synthesis of starting materials for the process of the invention shown as step (c). Thus, step (a) is not necessary for the practice of the invention.

In step (a) of Reaction Scheme 1, an anthranilic acid of formula (IV) is reacted with a carbonyl source such as phosgene to yield an isatoic anhydride of formula (V). Anthranilic acids of formula (IV) are commercially available or may be synthesized according to literature references. Step (a) can be carried out as described in German Patent 500,916 and Friedl. 17, 500 (1930) as described by R. H. Clark et al. in the Journal of Organic Chemistry, Vol. 9, pp. 55-67 (1943). Alternatively, commercially available isatoic acids of formula (V) may be used or formula (V) compounds may be synthesized as otherwise described in the art.

In step (b) of Reaction Scheme 1, the isatoic anhydride (V) is reacted with an N,O-dialkylhydroxylamine of the formula HN(OAlk$^1$)Alk$^2$, with an important example being N,O-dimethylhydroxylamine hydrochloride. The reaction may be conducted at a temperature of about 25° to 100° C. in a solvent such as ethanol, in the presence of a base such as triethylamine if an acid addition salt of HN(OAlk$^1$)Alk$^2$ is used. Publications describing compounds of the formula HN(OAlk$^1$)Alk$^2$ include Weinreb and Boutin, R. H.; Rapoport, H. *J.O.C.* 51, 5320, (1986) and Cupps, T. L.; Boutin, R. H.; Rapoport, H. *J.O.C.* 50, 3972, (1985).

In step (c) of Reaction Scheme 1, the anthranilic acid amide of formula (II), e.g. an N-alkoxy-N-alkyl anthranilic acid is reacted with a halobenzene of formula (III) in the presence of an alkyllithium to yield the 2-aminobenzophenone of formula (I) as described above. The halobenzene (III) may be obtained commercially or may be synthesized according to literature references such as H. G. Fletcher in Methods Carbohydr. Chem. 1963, II 166; by R. F. Cunico et al in J. Org. Chem. 1980, 45, 4797; and by L. J. Mathias in Synthesis 1979, 561. Recovery and purification of the product (I) may be by techniques known in the art including crystallization and column chromatography.

Preferably, the halobenzene of formula (III) does not have an electrophilic substituent ortho to the incipient anion, i.e. the location of Hal on the ring, or an acidic hydrogen or an ortho chloro or ortho- or para-nitro substituent since yields tended to diminish in such cases. In addition, if $X^1$ or $X^2$ is to be hydroxy, it will usually be protected before step (c) and deprotected after the reaction, e.g. with a benzyl or t-butyl diphenyl silyl group.

Also part of the present invention are novel intermediates including those of formula (II).

In the following examples and throughout the specification, the following abbreviations may be used: g (grams); ml (milliliters); mmol (millimoles); min (minutes); N (normal); b.p. (boiling point); m.p. (melting point); Ph (phenyl); Bu (butyl); and EtOAc (ethyl acetate). Unless otherwise indicated, all temperatures are reported in °C. (degrees Centigrade) and pressure in mm of Hg (millimeters of mercury).

EXAMPLE 1

(a) To a solution of N,O-dimethylhydroxylamine hydrochloride (51.2 g, 0.53 mmol) in 90-95% aqueous ethanol (200 ml) is added triethylamine (53 g, 0.53 mmol) and, after 10 minutes stirring at 25° C., isatoic anhydride (37.0 g, 0.35 mmol) in portions. The reaction is then heated at reflux for 1.5 hrs and poured onto an equal volume of ice and saturated sodium bicarbonate. The ethanol is then removed by rotary evaporation, the resulting aqueous mixture extracted with ethyl acetate (3×150 ml), the combined extracts washed with water, brine, dried over magnesium sulfate and activated charcoal, and concentrated to an orange oil. The oil is chromatographed on silica gel (1:1 diethyl ether: hexanes, then acetone) and distilled to give N-methoxy-N-methyl anthranilic acid amide as a pale yellow oil; yield 47.4 g (75%); b.p. 148°-151° C./0.35 mm.

| Elemental Analysis for C₉H₁₂N₂O₂ | | | |
|---|---|---|---|
| | % C | % H | % N |
| Found: | 59.72 | 6.78 | 15.47 |
| Calculated: | 59.99 | 6.71 | 15.55 |

(b) To a mixture of N-methoxy-N-methyl anthranilic acid amide prepared as in Example 1(A)(2.00 g, 11.1 mmol) and 4-benzyloxy-bromobenzene (2.92 g, 11.1 mmol) in anhydrous tetrahydrofuran (65 ml) at −78° C. under nitrogen is added, with vigorous stirring, n-BuLi in hexanes (13.8 ml, 1.6M, 22.2 mmol) at 0.60 ml/min. After 20 min, aqueous hydrochloric acid is added (1N, 20 ml), the mixture extracted with ethyl acetate (150 ml), ethyl acetate washed with water, brine, dried over magnesium sulfate, and concentrated. Recrystallization from hexanes gave 4'-benzyloxy-2-aminobenzophenone as yellow crystals; yield: 2.35 g, (70%); m.p. 99°–101° C.

| Elemental Analysis for C₂₀H₁₇NO₂: | | | |
|---|---|---|---|
| | % C | % H | % N |
| Found: | 79.12 | 5.66 | 4.54 |
| Calculated: | 79.18 | 5.65 | 4.62 |

EXAMPLES 2–17

Following the procedure of Example 1(b) and substituting an equimolar amount of the appropriate aryl bromide for 4-benzyloxy-bromobenzene, the desired 2-aminobenzophenones were obtained as indicated in the following Table 1. In Table 1, compounds recovered as oils were purified by column chromatography using silica gel and a mixture EtOAc and hexanes as the eluant.

TABLE I

Products of Formula (I) where $X^1$ = H, r = 1 and s = 1

| | X² | Temp. | Yield | M.P. | Calculated C | Calculated H | Calculated N | Found C | Found H | Found N |
|---|---|---|---|---|---|---|---|---|---|---|
| 1 | p-OCH₂Ph | −78 | 70% | 99–101 | 79.19 | 5.65 | 4.62 | 79.12 | 5.66 | 4.54 |
| 2 | H | −78 | 70 | 103–104 | 79.16 | 5.62 | 7.10 | 79.09 | 5.63 | 7.06 |
| 3 | o-CH₃ | −78 | 55 | 79–81 | 79.60 | 6.20 | 6.63 | 79.53 | 6.24 | 6.62 |
| 4 | m-CH₃ | −78 | 70 | 68–69 | 79.60 | 6.20 | 6.63 | 79.47 | 6.25 | 6.61 |
| 5 | p-CH₃ | −78 | 68 | 91–92 | 79.60 | 6.20 | 6.63 | 79.43 | 6.25 | 6.59 |
| 6 | o-OCH₂Ph | −78 | 68 | 108–109 | 79.19 | 5.65 | 4.62 | 79.09 | 5.64 | 4.62 |
| 7 | m-OCH₂Ph | −78 | 67 | 106–107 | 79.19 | 5.65 | 4.62 | 78.89 | 5.70 | 4.61 |
| 8 | o-CH₂OSiPh₂t-Bu | −78 | 47 | oil | 77.38 | 6.71 | 3.01 | 77.20 | 6.74 | 2.95 |
| 9 | m-CH₂OSiPh₂t-Bu | −78 | 50 | oil | 77.38 | 6.71 | 3.01 | 77.44 | 6.73 | 3.00 |
| 10 | p-CH₂OSiPh₂t-Bu | −78 | 50 | 106–108 | 77.38 | 6.71 | 3.01 | 77.28 | 6.74 | 3.00 |
| 11 | m-Cl | −100 | 51 | 79–80 | 67.40 | 4.35 | 6.05 | 67.31 | 4.38 | 6.00 |
| 12 | p-Cl | −100 | 55 | 100–102 | 67.40 | 4.35 | 6.05 | 67.33 | 4.39 | 6.01 |
| 13 | o-F | −100 | 35 | 124–125 | 72.55 | 4.68 | 6.51 | 72.45 | 4.71 | 6.48 |
| 14 | m-CN | −100 | 34 | 114–115 | 75.66 | 4.54 | 12.60 | 75.57 | 4.56 | 12.53 |
| 15 | p-CN | −100 | 40 | 157–159 | 75.66 | 4.54 | 12.60 | 75.39 | 4.59 | 12.51 |
| 16 | m-CO₂t-Bu | −100 | 52 | 129–130 | 72.71 | 6.44 | 4.71 | 72.60 | 6.47 | 4.69 |
| 17 | p-CO₂t-Bu | −100 | 51 | oil | 72.71 | 6.44 | 4.71 | 72.74 | 6.47 | 4.68 |

EXAMPLES 18–22

Typical Compounds of formula (I) which may be prepared in accordance with the present invention include those of Table II:

TABLE II

| | X¹ | R position | X² | s | position |
|---|---|---|---|---|---|
| 18 | Cl | 1 | 4 | H | 1 | — |
| 19 | H | 1 | — | CH₃ | 2 | o,p |
| 20 | CF₃ | 1 | 6 | Cl | 1 | m |
| 21 | OCH₃ | 2 | 4,5 | H | 1 | — |
| 22 | H | 1 | — | CF₃,Cl | 2 | o,p |
| 23 | | | | | | |

What is claimed is:

1. An anthranilic acid amide of the following formula (II):

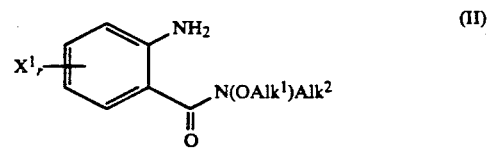

wherein $X^1$ is independently hydrogen, trifluoromethyl, cyano, hydroxy, loweralkyl, chlorine, fluorine, loweralkylthio, loweralkoxy, —Y—COOR¹ or —Y—NR²R³;

Y is a direct bond or a C₁₋₄ linear or branched divalent alkyl;

R¹ is loweralkyl, cycloloweralkyl, substituted or unsubstituted phenyl or substituted or unsubstituted phenylloweralkyl wherein the phenyl or phenylloweralkyl substitutents may be 1 or 2 of chlorine, fluorine, loweralkyl, loweralkoxy, nitro or trifluoromethyl;

R² and R³ are independently a value of R¹;

r is 1 or 2; and

Alk¹ and Alk² are independently C₁₋₄ alkyl or are joined to each other to form a 5–7 membered saturated ring with the nitrogen and oxygen atoms to which they are attached.

2. The amide of claim 1, wherein X¹ is hydrogen or chlorine and r is 1.

3. The amide of claim 2, wherein X¹ is chlorine.

4. The amide of claim 1, wherein Alk¹ and Alk² are methyl.

5. The amide of claim 1, wherein X¹ is hydrogen or chlorine, r is 1 and Alk¹ and Alk² are methyl.

* * * * *